(12) United States Patent
Nikitin et al.

(10) Patent No.: US 8,125,634 B1
(45) Date of Patent: Feb. 28, 2012

(54) OPTICAL ADDITIVE SOLC FILTER FOR DEEP ULTRAVIOLET APPLICATIONS

(75) Inventors: Sergei Nikitin, Springfield, VA (US); Charles K Manka, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 337 days.

(21) Appl. No.: 12/512,161

(22) Filed: Jul. 30, 2009

(51) Int. Cl.
*G01J 3/44* (2006.01)

(52) U.S. Cl. .................. 356/301; 250/458.1; 250/461.1; 356/73; 356/128; 356/417

(58) Field of Classification Search .................. 250/46.1, 250/458.1, 461.1; 382/73, 301, 318, 417, 382/128; 356/73, 301, 318, 417, 128
See application file for complete search history.

(56) References Cited

U.S. PATENT DOCUMENTS

| | | | | |
|---|---|---|---|---|
| 4,847,198 A | * | 7/1989 | Nelson et al. ................. | 356/301 |
| 7,286,222 B2 | * | 10/2007 | Gardner, Jr. ................. | 356/301 |
| 7,436,510 B2 | | 10/2008 | Grun et al. | |

OTHER PUBLICATIONS

H.A. Tarry "Electrically tunable narrowband optical filter" Electron. Lett. vol. 11 Issue 19 p. 471-472 (Sep. 1975).
M. Razeghi, "Short-Wavelength Solar-Blind Detectors—Status, Prospects and Markets" Proceedings of IEEE V. 90, No. 6, pp. 1006-1014 (2002).
S. A. Asher, "UV Resonance Raman Spectroscopy for Analytical, Physical and Biophysical Chemistry Part 1", Analytical Chemistry V. 65, No. 2, pp. 59A-66A (1993).
I. Solc "Birefringent chain filters" JOSA V. 55, p. 621 (1965).
A.Yariv and P.Yeh, "Optical Waves in Crystals", Wiley Classics Library Edition, ISBN 0-471-43081-1, pp. 131-143 (2003).
R.C Jones, "New calculus for the treatment of optical systems", JOSA V. 31, p. 488 (1941).
S. A. Asher, "UV Resonance Raman Spectroscopy for Analytical, Physical, and Biophysical Chemistry Part 2", Analytical Chemistry, vol. 65, No. 4 (2003).

* cited by examiner

*Primary Examiner* — Gregory J Toatley
*Assistant Examiner* — Iyabo S Alli
(74) *Attorney, Agent, or Firm* — Amy L. Ressing; L. George Legg (57) ABSTRACT

An additive Šolc filter (ASF) includes i) a first polarizer for receiving an input light, such as from a monochromatic light source, and transmitting a first polarized output, ii) at least one birefringent plate positioned to receive the first polarizer output and transmit an output with wavelength-dependent polarization state, and iii) a second polarizer for receiving the plate output and transmitting a second polarized, filtered output. An ASF spectroscopy system includes the ASF; a monochromatic light source input, e.g. a laser; a sample chamber for exposing a sample to the second polarized, tuned output and generating a signal characteristic of the sample that is filtered by the ASF; and a detector for acquiring the characteristic signal.

15 Claims, 8 Drawing Sheets

OPTICAL ADDITIVE ŠOLC FILTER FOR DEEP ULTRAVIOLET APPLICATIONS

TECHNICAL FIELD

The invention is directed to a notch filter for spectroscopy. More particularly, the invention is directed to a spectroscopic system employing an additive Šolc filter.

BACKGROUND OF THE INVENTION

A number of optical applications in the deep ultra violet (DUV) range have limitations due to the absence of simple and reliable optical notch filters. A "notch" filter is one that blocks a narrow wavelength region and transmits other wavelengths.

This is particularly limiting since the DUV optical range is an interesting range and fruitful for a number of remote sensing applications that take advantage of "solar blind measurements". e.g. as described in M. Razeghi, "Short-Wavelength Solar-Blind Detectors—Status, Prospects and Markets" *Proceedings of IEEE* V. 90, No 6, pp. 1006-1014 (2002) where relatively high atmospheric transmission is combined with virtually no solar background light (blocked by ozone layer in upper atmosphere).

Such a filter could be used to suppress elastically scattered light (Raleigh or diffuse scattering from a sample) in ultraviolet resonance Raman (UVRR) diagnostics, e.g. as described in S. A. Asher, "UV Resonance Raman Spectroscopy for Analytical. Physical and Biophysical Chemistry", *Analytical Chemistry* V. 65. No 2. pp 59A 66A, 201A-210A (1993). One such diagnostic, Swept Wavelength Optical Resonance Raman Diagnostic (SWORRD), is described in Grun et al., U.S. Pat. No. 7,436,510, issued Oct. 14, 2008, and incorporated herein by reference. An effective notch filter would allow the use of compact single-stage spectrometers for data acquisition. However, a limited choice of optically transparent materials in the DUV range is a considerable obstacle to the design of interferometric filters or acousto-optical tunable notch filters for wavelengths shorter than 300 nm.

A birefringent filter design originally proposed by Šolc, described in 1. Šolc "Birefringent chain filters" *JOSA* V. 55, p. 621 (1965), and incorporated herein by reference, is suitable for DUV applications. Such Šolc filter includes two typical configurations, fan and folded. A detailed description of both types of Šolc filters and analysis of their spectral transmission can be found in A. Yariv and P. Yeh, "Optical Waves in Crystals" Wiley Classics Library Edition, ISBN 0-471-43081-1, pp 133-154 (2003), which is based on Jones matrix formalism, described in R. C Jones, "New calculus for the treatment of optical systems", *JOSA* V. 31, p. 488 (1941). These designs, however, are exclusively for narrow-line transmission (<1 nm), rather than for rejection (or blocking) of narrow linewidths.

It would be desirable to provide an optical filter to remove these limitations.

BRIEF SUMMARY OF THE INVENTION

According to the invention, an additive Šolc filter (ASF) includes i) a first polarizer for receiving an input light, such as from a monochromatic light source, and transmitting a first polarized output, ii) at least one birefringent plate positioned to receive the first polarizer output and transmit an output with wavelength-dependent polarization state, and iii) a second polarizer for receiving the plate output and transmitting a second polarized, filtered output. An ASF spectroscopy system includes the ASF: a monochromatic light source input, e.g. a laser; a sample chamber for exposing a sample to the second polarized, tuned output and generating a signal characteristic of the sample that is filtered by the ASF; and a detector for acquiring the characteristic signal.

The additive Šolc filter ("ASF") is suitable for narrow-line rejection (<1 nm), as dictated by the needs of UVRR and other applications. A few birefringent materials have excellent DUV transmission and could be used to construct such a filter (e.g. crystal quartz, sapphire or magnesium fluoride). Such a filter is particularly useful for applications in the 190 to 250 nm range, where alternative filters are inefficient or simply do not exist. The ASF can also provide blocking of one or more particular wavelengths and have a desired spacing between the blocked wavelengths. The ASF is especially advantageous for multi-wavelength and/or wavelength-tunable applications such as SWORRD [Grun et al., above], since a single ASF can be used at a sequence of wavelengths. All other improvements applicable to a regular Šolc filter are also applicable to ASF (e.g. Šolc filters can be modified to allow an extended field-of-view or implement tunability by using an external electric field, as described in H. A. Tarry, "Electrically tunable narrowband optical filter" *Electronics Letters* V. 11, p 471. Slight tuning of the filter can be accomplished by tilt, temperature or external electric field. The ASF is shown to provide sufficient contrast to acquire the Raman spectrum of a highly scattering sample (such as Teflon) using a single stage grating spectrograph simultaneously for both Stokes and anti-Stokes regions. An ASF allows integration into the fiber Raman probe, which is particularly useful for applications in the field that typically employ surface illumination and collection of the backscattered Raman signal.

BRIEF DESCRIPTION OF THE DRAWINGS

FIG. 7 shows the measured transmission spectra for the Šolc filter (FIG. 7A) and for the ASF (FIG. 7B);

DETAILED DESCRIPTION OF THE INVENTION

A Šolc filter is formed by an in-line arrangement of optically transparent birefringent plates of properly chosen material, thickness and orientation of optic axis with respect to each other, placed between optical polarizers located at either end of the arrangement. There are two types of Šolc filter designs: fan and folded. Azimuth angles for optical components of the simplest Šolc filters of both types are summarized in Table 1. The angle $\rho=45°/N$ is determined by the number of plates N.

TABLE 1

Arrangement of optical components in fan and folded Šolc filters

| | Filter type | |
| --- | --- | --- |
| Element | Fan Azimuth angle | Folded Azimuth angle |
| Entrance polarizer | 0° | 0° |
| Plate 1 | ρ | ρ |
| Plate 2 | 3ρ | −ρ |
| Plate 3 | 5ρ | ρ |
| Plate 4 | 7ρ | −ρ |
| Plate N | (2N−1)ρ | $(-1)^N \rho$ |
| Exit polarizer | 0° | 90° |

In a folded Šolc filter the transmitted wavelength is rotated by 90°, while in a fan Šolc filter the polarization of the transmitted wavelength is preserved. For both filter types, a set of properly oriented birefringent plates alters the polarization of a few "special" wavelengths, so that these "special" wavelengths are selectively transmitted by a polarizer placed at the output of the filter. This arrangement is required for use of a Šolc filter as a "narrow-line" transmission filter.

Figure 1:
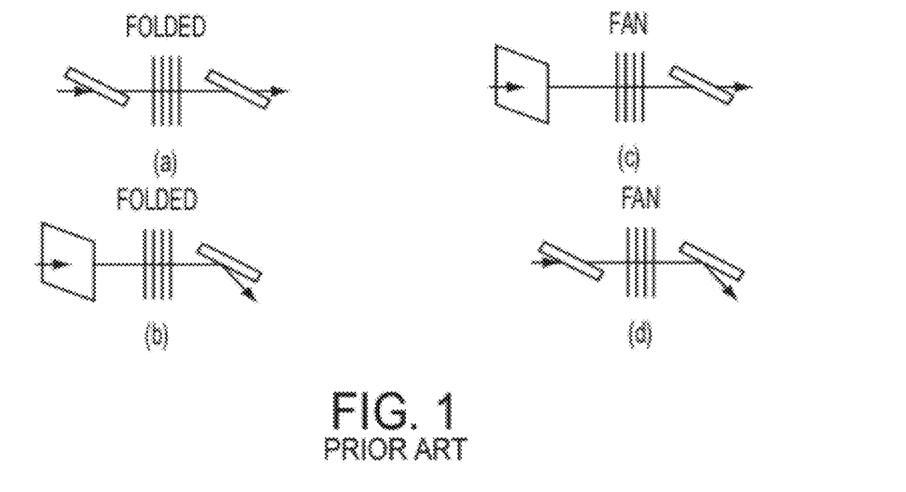
FIG. 1 is a Šolc filter.

The ASF is "additive" to the Šolc filter in a sense that it is a narrow-line rejection filter. This additive operation mode is achieved if either the output polarizer is rotated orthogonally to its position in a Šolc filter: or, if the output polarizer (such as a polarizing beamsplitter) produces two orthogonally polarized outputs, in which case the alternative output of the filter is used. FIG. 1 depicts arrangements where such operation is possible: (a) Folded-transmitted, (b) Folded-reflected, (c) Fan-transmitted and (d) Fan-reflected geometries. Table 1 includes the relative orientations of both fan and folded birefringent plate assemblies.

The full width at half maximum (FWHM) of the very narrow rejected spectral range (notch) depends on filter design and is generally comparable to the FWHM for interferometric notch filters. In our implementation of the ASF a folded geometry is used, since the ASF based on this geometry preserves the polarization state of transmitted light, a preferred arrangement for the experimental tests. However, similar performance can be achieved with fan geometry.

To illustrate why certain "special" wavelengths are rejected by the ASF, consider the simplest case, when all birefringent plates are made of the same uniaxial birefringent material, have the same thickness and are arranged in a folded geometry. Due to the optical dispersion, the optical phase retardation of the plates is wavelength dependent, and can be calculated if the plate thickness is known. For crystal quartz, the following Laurent series equations can be used:

$$n = \sqrt{A_0 + A_1 \lambda^2 + A_2/\lambda^2 + A_3/\lambda^4 + A_4/\lambda^6 + A_5/\lambda^8}$$

where coefficients for $n_e$ are:

$A_0 = 2.3849; A_1 = -1.259E - 2; A_2 = 1.079E - 2;$ $A_3 = 1.6518E - 4; A_4 = -1.94741E - 6; A_5 = 9.36476E - 8$ and for $n_o$ are:

$A_0 = 2.35728; A_1 = -1.17E - 2; A_2 = 1.054E - 2;$ $A_3 = 1.34143E - 4; A_4 = -0.445368E - 6; A_5 = 5.92362E - 8.$

If the wavelength of light propagating through the filter is such that each plate introduces half-wavelength retardation $\delta=2\pi(m_i+1/2)$, where $m_i$ is the retardation order of the plate, each plate preserves the linear polarization of light, but it "mirrors" the direction of polarization with respect to the plate axis. For these specific wavelengths, the polarization of light through each element of the filter can be easily traced. For example, Table 2 traces the polarization of light through a folded six plate ASF (specific example used in our tests). As can be seen, these specific wavelengths are rejected by the exit polarizer. These are the "notch" wavelengths of the filter.

TABLE 2

Polarization states of light after different components of a folded Šolc filter made of six plates (ρ = 7.5°).

| Element | Azimuth angle | Input polarization | Output polarization |
| --- | --- | --- | --- |
| Entrance polarizer | 0 | 0 | transmitted |
| Plate 1 | ρ | 0 | 2ρ (+15°) |
| Plate 2 | −ρ | 2ρ (+15°) | −4ρ (−30°) |
| Plate 3 | ρ | −4ρ (−30°) | 6ρ (+45°) |
| Plate 4 | −ρ | 6ρ (+45°) | −8ρ (−60°) |
| Plate 5 | ρ | −8ρ (−60°) | 10ρ (+75°) |
| Plate 6 | −ρ | 10ρ (+75°) | −12ρ (−90°) |
| Exit polarizer | 0 | −90° | Blocked |

Recalling that $\delta=2\pi(n_o-n_e)L/\lambda$, where L is the plate thickness. $n_o-n_e$ is the difference between ordinary and extraordinary indices of refraction and λ is the optical wavelength in vacuum, the following approximate expression for the spacing between adjacent notch wavelengths can be obtained: $\Delta\lambda=\lambda^2/2L|n_o-n_e|$. Larger plate thickness L corresponds to closer spacing, $\Delta\lambda$. It is the individual plate thickness and birefringence $n_o-n_e$ that determine the notch wavelengths and the wavelength spacing between them.

For all other wavelengths, polarization of light after each plate and optical transmission of the ASF can be evaluated using Jones matrix formalism. Using this formalism, a birefringent plate introducing retardation phase δ and rotated by an angle ρ is described by a product of matrices: $\hat{W}(\delta,\rho)= \hat{R}(-\rho)\hat{W}(\delta)\hat{R}(\rho)$, where $$\hat{W}(\delta) = \begin{bmatrix} e^{-i\delta/2} & 0 \\ 0 & e^{i\delta/2} \end{bmatrix}$$

is a matrix of a birefringent plate and $$\bar{R}(\rho) = \begin{bmatrix} \cos\rho & \sin\rho \\ -\sin\rho & \cos\rho \end{bmatrix}$$

is a rotation operator. A polarizer lined up at azimuth angle 0 is described by the matrix $$\hat{P}_x = \begin{bmatrix} 1 & 0 \\ 0 & 0 \end{bmatrix}$$

A matrix for the entire ASF is described by a product of each component's matrix:

$$\hat{S}=\hat{P}_x\hat{W}(\rho,\delta)\hat{W}(-\rho,\delta)\hat{W}(\rho,\delta)\ldots\hat{W}(-\rho,\delta)\hat{W}(\rho,\delta)\hat{W}(-\rho,\delta)\hat{P}_x$$

E-field polarization components at the input and at the output of the system are then given by:

$$\begin{pmatrix}E_{2x}\\E_{2y}\end{pmatrix}=\hat{S}\begin{pmatrix}E_{1x}\\E_{1y}\end{pmatrix}$$

and the overall transmission of the filter is $$T=\frac{|E_{2x}|^2+|E_{2y}|^2}{|E_{1x}|^2+|E_{1y}|^2}.$$

Figure 2:
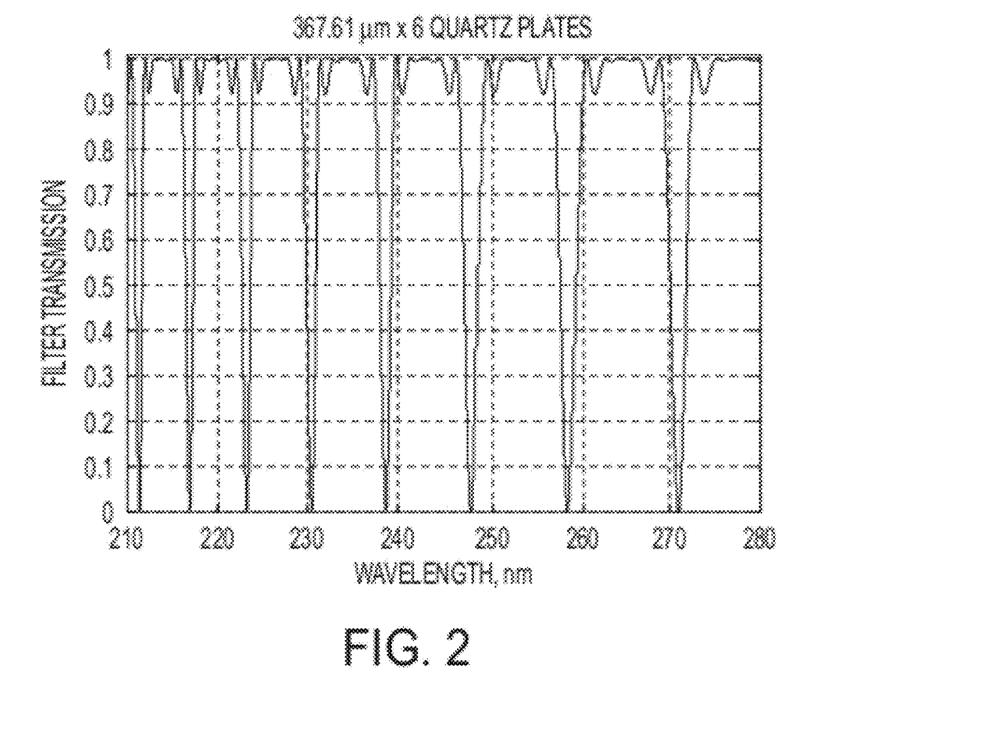
FIG. 2 is a graph of a transmission calculation for a folded ASF; designed specifically to block 248 nm, and providing blocking at many other wavelengths as well.

An example of such a transmission calculation for a folded ASF is shown in the graph in FIG. 2 for the case of a folded ASF based on six quartz plates, each 367.6 μm thick, for the range of 210-280 nm. Surface losses and material absorption are neglected.

Figure 3:
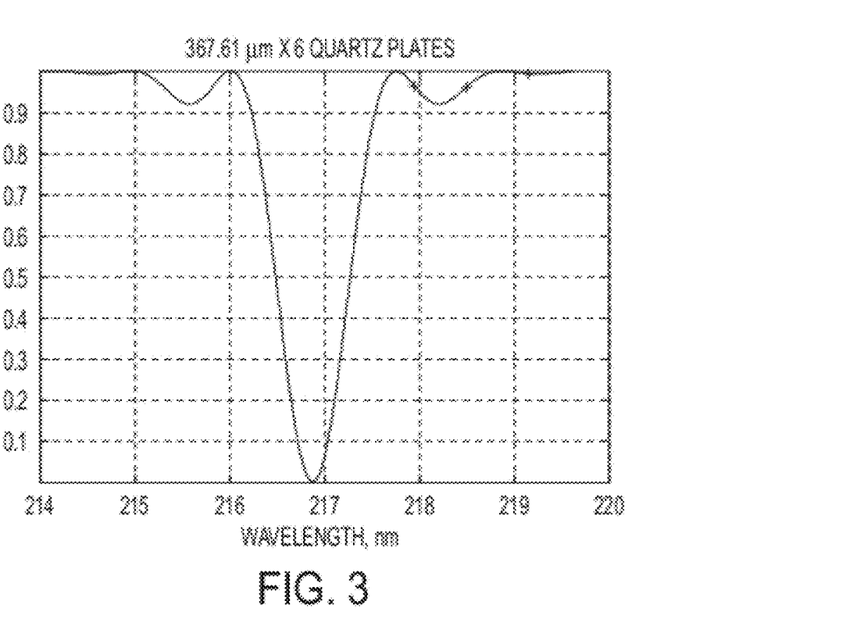
FIG. 3 is a graph showing ASF transmission (in percents) for one of the blocked wavelengths on an expanded scale.

For wavelengths at which the individual birefringent plates act as half or full wave plates, the transmitted light remains linearly polarized after transmission through each plate. For all other wavelengths, the transmitted light becomes elliptically polarized with the orientation of the major axis rotated and the eccentricity changed after each plate. For most of the interval between blocked wavelengths, the final polarization ellipse after transmission through the last plate has the major axis rotated by a small angle and the eccentricity near one. This variation accounts for the structure of the transmission between blocked wavelengths. Table 3 shows the polarization state of light after different components of a folded ASF made of six plates ($\rho=7.5°$) described by the polarization ellipse: $\phi$ is the rotation angle of its major axis and $\epsilon$ is its eccentricity. T is ASF transmission in percents, and illustrates this effect for the wavelengths marked in FIG. 3, i.e. for $\lambda=217.95$ nm (A). $\lambda=218.50$ nm (B) and $\lambda=219.15$ nm (C). It is an expanded view for the transmission minimum at ~217 nm corresponding to $m_i=20$. Marks (+) are placed for wavelengths 217.95 nm (A), 218.50 nm (B) and 219.15 nm (C).

TABLE 3

Polarization states for light of different wavelengths

| | A | | B | | C | |
|---|---|---|---|---|---|---|
| | $\lambda=217.95$ T = 96.361% | | $\lambda=218.50$ T = 96.113% | | $\lambda=219.15$ T = 99.362% | |
| | $\phi$, deg | E | $\phi$, deg | E | $\phi$, deg | E |
| Plate 1 | 10.9 | 0.993 | 6.66 | 0.991 | 2.23 | 0.996 |
| Plate 2 | −9.2 | 0.937 | 2.39 | 0.974 | 3.15 | 0.999 |
| Plate 3 | −7.36 | 0.926 | −5.72 | 0.998 | 2.29 | 1.000 |
| Plate 4 | 11.6 | 0.989 | −4.09 | 1.000 | 0.15 | 0.994 |
| Plate 5 | −1.95 | 1.000 | 4.65 | 0.980 | −2.08 | 1.000 |
| Plate 6 | −9.82 | 0.996 | 5.89 | 0.985 | −3.15 | 0.998 |

The width of the notched wavelength region and height of secondary rejection peaks are determined by the number of plates. In practice, material absorption and Fresnel losses at optical surfaces reduce filter transmission and limit the overall number of birefringent plates that can be used. Additional factors that restrict the number of plates are limitations on angular field of view and overall filter length. Optical transmission can be improved, if anti-reflection coatings are used or the birefringent plates are immersed into an index-matching fluid (for quartz, decahydronaphtalene (Decalin), which has refractive index n=1.48 or fluorocarbon FC-104, 3M™, refractive index n=1.27 could be used).

Figure 4:
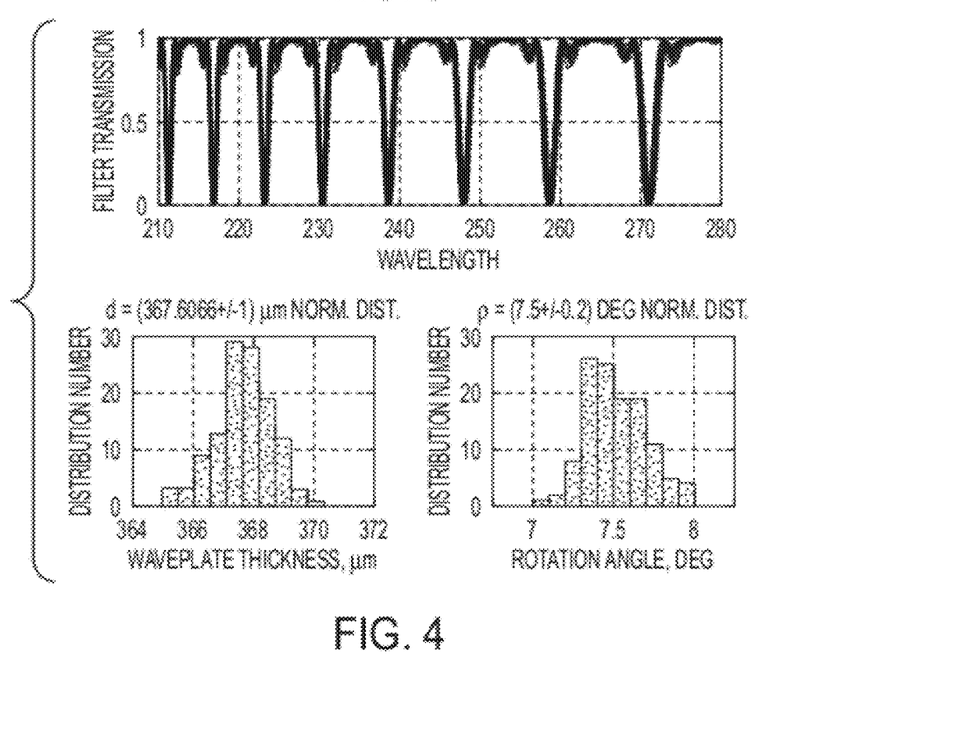
FIG. 4 shows numerical simulations for a six plate ASF design incorporating reasonably anticipated assembly errors for the selected plate azimuth angles (ρ) and manufacturing errors for thicknesses (d)

Manufacturing and assembly errors degrade filter performance since they affect ASF transmission at the main minima and the minima position. A number of numerical simulations based on the Jones matrix formalism were made for this particular six plate ASF design with randomized variation of the plate's azimuth angles ($\rho$) and thicknesses (d) to evaluate filter performance degradation due to these errors. An example of such simulation is shown in FIG. 4. It shows simulation results for 20 different six plate ASFs similar to the one shown in Graph. 1 and assembled with thickness tolerance $\delta d=1$ μm RMS: and azimuth angle tolerance $\delta\square=0.2°$ RMS.

From these simulations it is observed that:

d—errors decrease filter performance at shorter wavelengths more than at longer wavelengths because the same thickness error corresponds to a larger retardation phase error.

$\rho$—errors decrease filter performance uniformly over the whole spectral range of calculation For d=367.6 μm used here, the manufacturing tolerance on plate thickness required to achieve performance reasonably close to the theoretical limit is ~0.2 μm RMS. Since for quartz at these wavelengths $|n_o-n_e|\sim 0.011$, this is equivalent to ~0.06 rad phase retardation error for each plate. Therefore, very reasonable assembly accuracy of 1° is sufficient to achieve >100:1 contrast.

Figure 5:
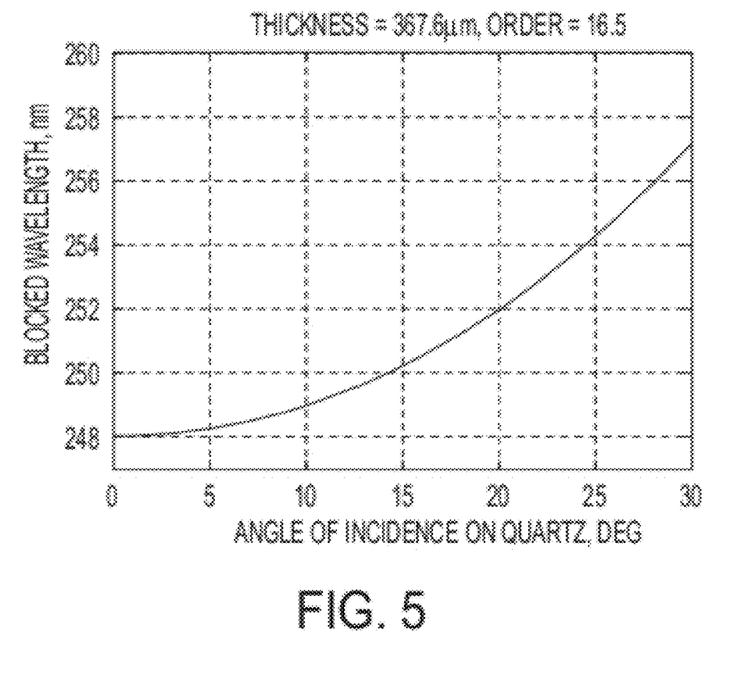
FIG. 5 is a calculated tuning curve for a tilted ASF at a specific blocked wavelength.

Since phase retardation depends on the thickness of the plate, the position of the notch wavelengths changes with the propagation path determined by plate thickness and/or tilt. Therefore, it is possible to achieve a modest tuning of the filter by changing its tilt angle. A calculated tuning curve for a tilted filter is shown in FIG. 5. It shows ASF tuning by tilting it from the normal incidence. The calculation is an approximation, where optical path variation due to difference between $n_o$ and $n_e$ is neglected. Alternatively, a similar tuning result can be achieved by temperature variation, or application of an external E-field, which affects $|n_o-n_e|$.

Figure 6:
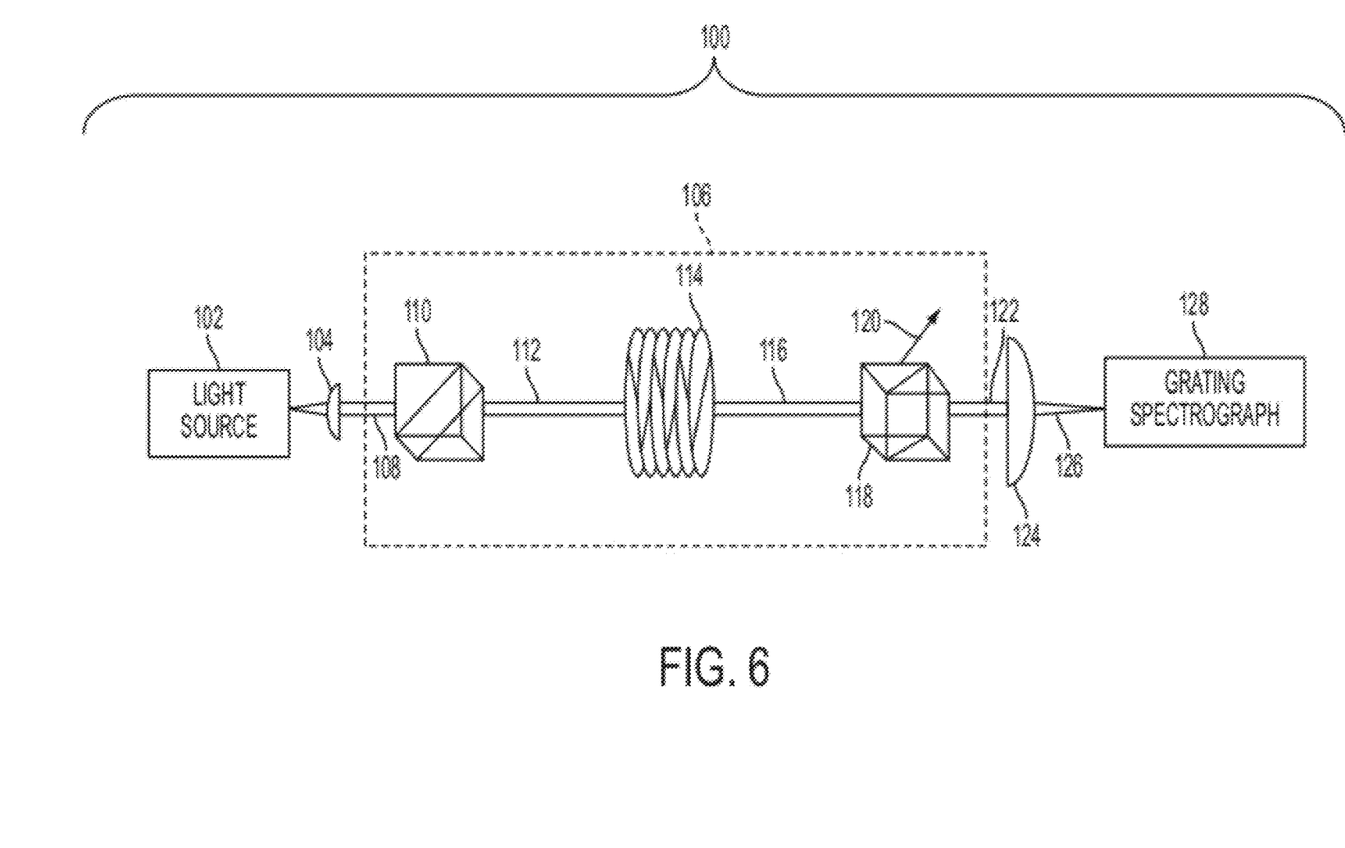
FIG. 6 is a diagram of the ASF experiment arrangement for transmission tests.
Figure 7A:
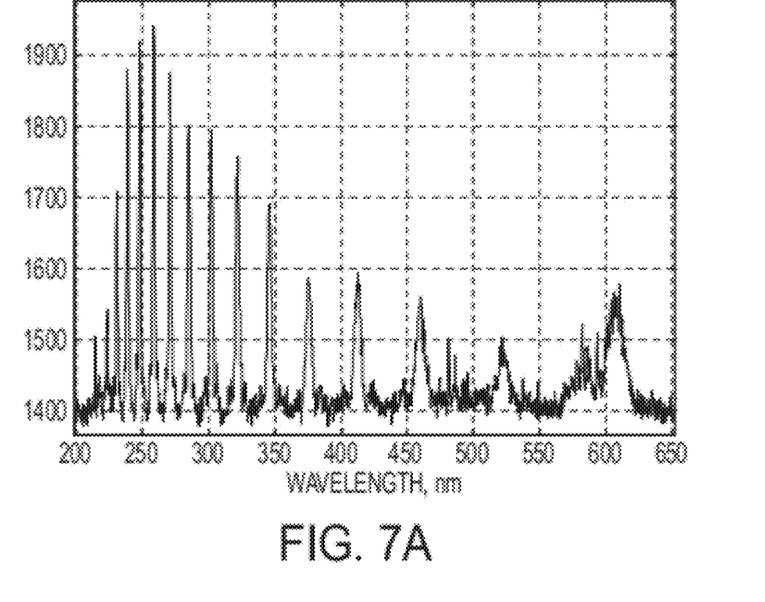
Figure 7B:
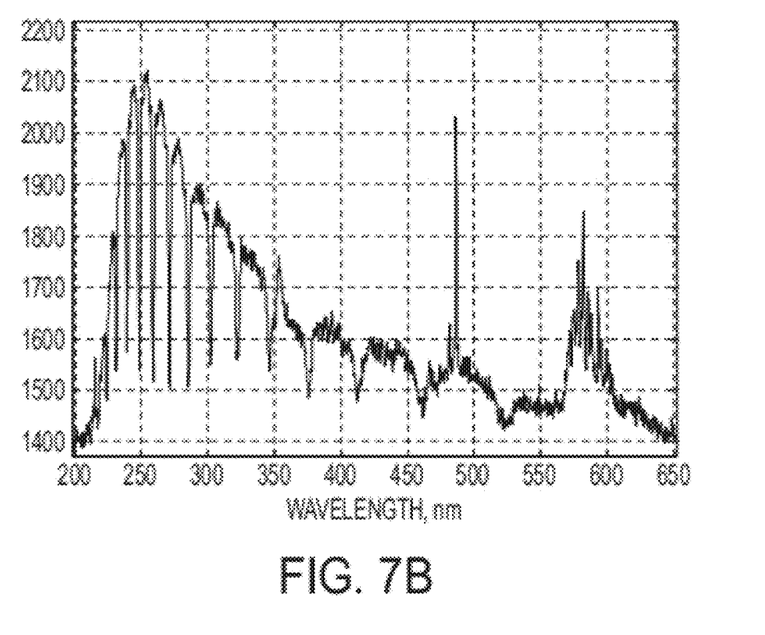

FIG. 6 illustrates an ASF assembly 106 according to the invention and test configuration 100 including, as shown, a light source 102 and collimating lens 104 providing multi-spectral light 106 input to an additive Šolc filter (ASF) 108. The ASF experimental configuration includes, as shown, an input polarizer 110 providing a beam of linearly polarized light 112, a stack of at least one (six as shown) quartz plates 114 manually positioned with relative orientations as per Table 2 with $\rho=7.5°$. The output from these plates 116, now a combination of linear and elliptical polarized light depending on wavelength, is passed through a polarizing beam splitter cube 118 where selected (designed) wavelengths are rejected 120 while the remaining wavelengths 122 are passed through a fused silica lens 124 and are focused 126 onto the slit of a grating spectrograph 128. The uncoated UV grade quartz plates had the following specifications: half-waveplate @ 248 nm, order N=16, retardation tolerance=$\lambda/200$. Glan-Thompson prisms made of alpha-BBO with specified extinction ratio exceeding $10^{-5}$ were used as broad-band UV polarizers. All optical components had 10 mm clear aperture. A calibrated deuterium arc lamp (Model number 63945, Newport/Oriel) was used as a broad-spectrum UV input source. Spectra transmitted by the ASF were acquired using a compact Ocean Optics spectrometer (model #HR4C142) having ~0.2 nm resolution in the DUV region. All acquired spectra were averaged over 100 independent measurements. Data were not corrected for spectrometer response. FIG. 7 shows the transmission spectra for a Šolc filter (FIG. 7A) and for the ASF (FIG. 7B). As can be seen in Table 4, the experimentally measured notch wavelengths demonstrate excellent agreement with the values, calculated from the quartz dispersion equations.

TABLE 4

Comparison of calculated and measured wavelengths for ASF transmission minima

| Order | Calc. minimum, nm | Meas. minimum, nm |
|---|---|---|
| 7  | 459.343359 | 461.1 |
| 8  | 412.125361 | 412.1 |
| 9  | 375.372082 | 375.5 |
| 10 | 346.023505 | 346.3 |
| 11 | 322.07773  | 321.7 |
| 12 | 302.182866 | 301.9 |
| 13 | 285.402832 | 285.2 |
| 14 | 271.075828 | 271.1 |
| 15 | 258.724991 | 258.9 |
| 16 | 248.00000  | 248.4 |
| 17 | 238.637583 | 239.1 |
| 18 | 230.434057 | 230.9 |
| 19 | 223.226556 | 223.9 |
| 20 | 216.880201 | 217.5 |
| 21 | 211.279988 | 211.6 |

Figure 8:
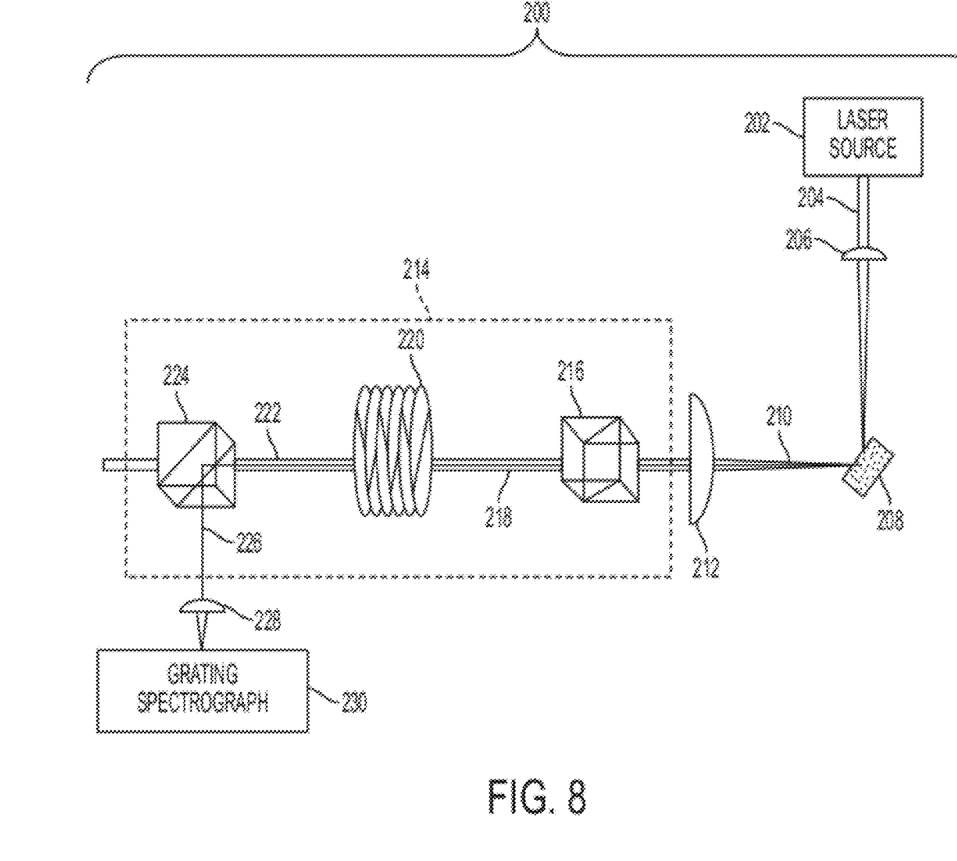
FIG. 8 is a schematic representation of a spectroscopy system employing the additive Šolc filter (ASF) according to the invention
Figure 9:
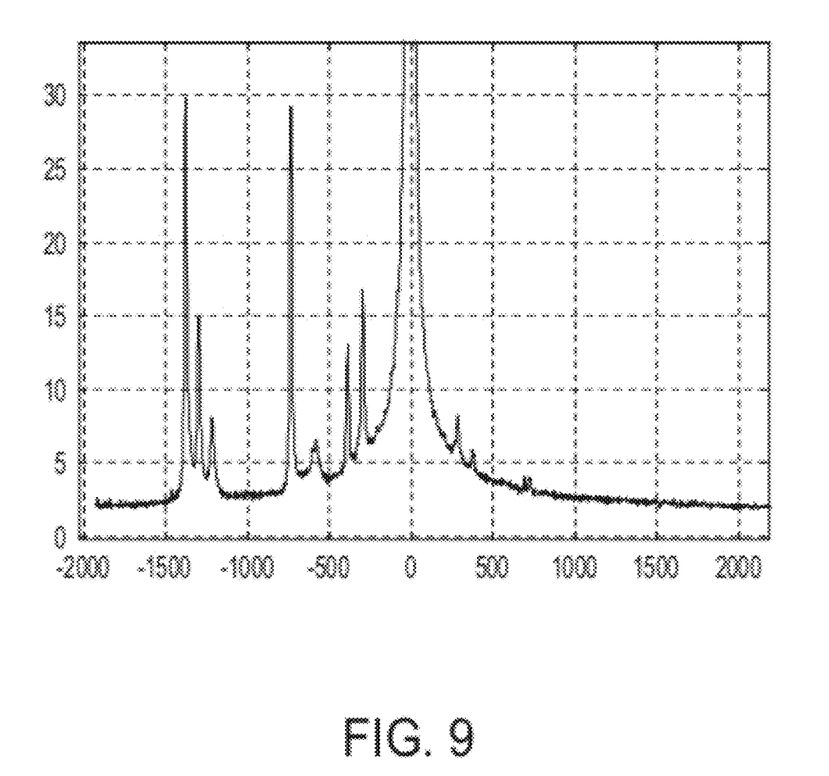
FIG. 9 is a graph showing an acquired Raman spectrum of Teflon by a single grating spectroscopy system according to the invention.

In order to demonstrate that an ASF has performance comparable to an interferometric filter, the ASF assembly and spectroscopy system as shown in FIG. 8 according to the invention was used to acquire a Raman spectrum of Teflon. As FIG. 8 illustrates an ASF assembly 214 according to the invention is incorporated in a spectroscopy system 200 having a laser light source 202 with wavelength set at 248.4 nm, matching one of the ASF measured transmission minima. Laser average power on the sample was ~4 mW. Laser output was linearly polarized with the E-field in the plane of scattering. Laser output 204 was focused with a fused silica lens 206 on the Teflon sample 208. Scattered light 210 from the Teflon sample, containing both shifted (Raman) and unshifted wavelengths, was collimated by a second fused silica lens 212 directing the scattered light from the sample through the ASF 214. The ASF 214 performs as previously described with the input polarizer 216 providing a linearly polarized beam 218. The quartz plate stack 220 (six as shown) produces a beam of elliptically and linearly polarized light 222 that is then incident on the polarizing beam splitting cube 224. At the final element 224 of the ASF the wavelength shifted light 226 is separated from the unshifted wavelengths and focused by a third fused silica lens 228 onto the entrance slit of grating spectrograph 230 equipped with a 2400 gr/mm grating and an Andor "Newton" CCD camera. Typical camera exposure time was ~300 sec. The light scattered from the teflon sample without wavelength shift was attenuated by the ASF by more than a factor of ~200 compared to the Raman shifted signal. An example of the acquired Raman spectrum of Teflon is shown in FIG. 9. As can be seen, both Stokes and anti-Stokes Raman bands shifted into the 200-1600 $cm^{-1}$ region are clearly seen. Though attenuated, the spectrally unshifted light still saturates the CCD, but blooming is not excessive. Intensities of anti-Stokes Raman bands at 291 $cm^{-1}$, 383 $cm^{-1}$ and 729 $cm^{-1}$ indicate sample temperature T~310K.

Figure 10:
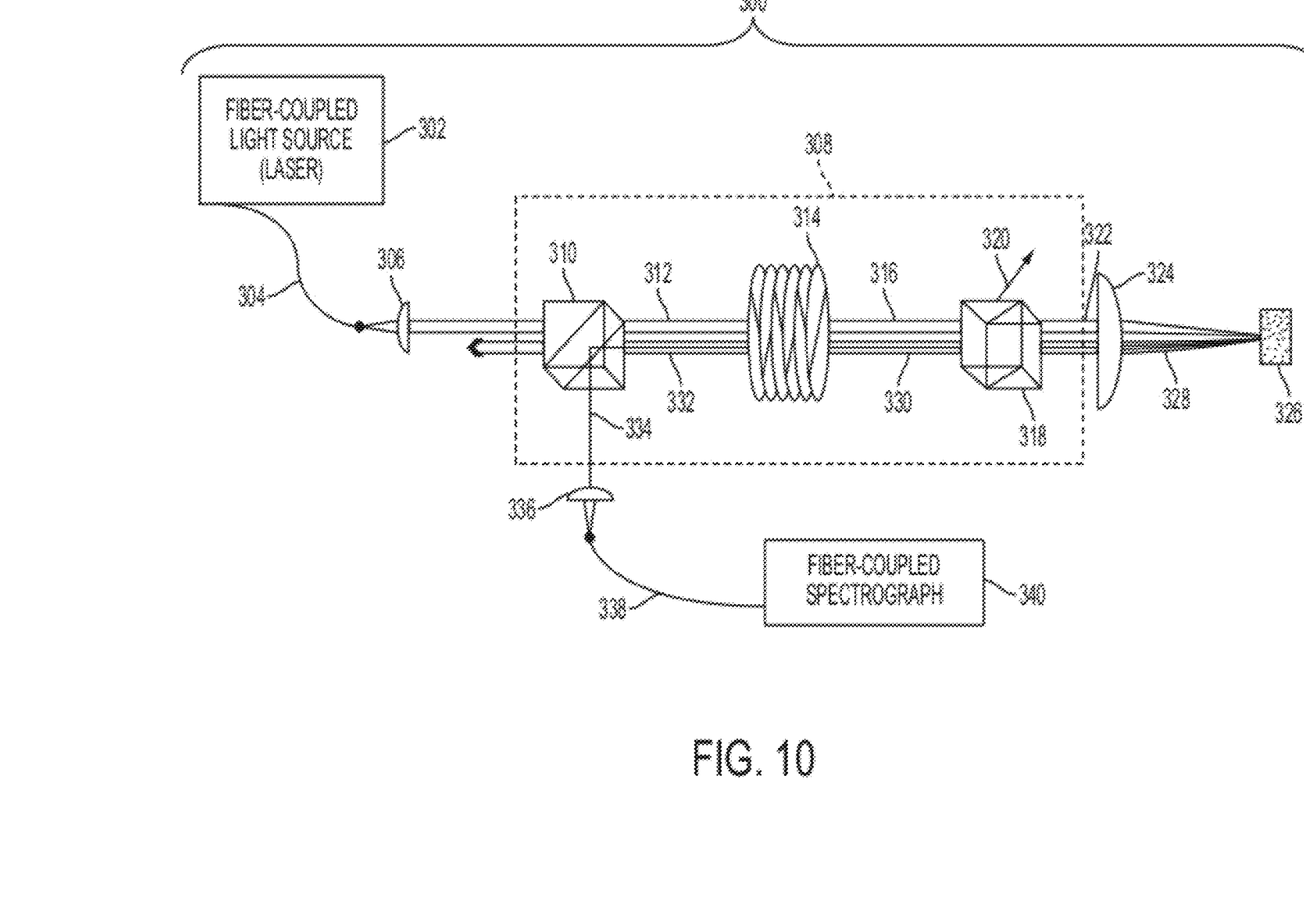
FIG. 10 is a schematic representation of a fiber coupled spectroscopy system employing an additive Šolc filter (ASF) according to the invention.

An ASF is very promising for configurations where both laser light illuminating sample and Raman signal are transported by optical fibers. Such a configuration is particularly useful for field applications, where a compact and simple arrangement is required. A typical Raman probe configuration involves surface illumination and collection of the backscattered Raman signal. An example of ASF use in such a configuration is shown in FIG. 10. The ASF shown in this configuration is similar to the one shown in FIG. 1(b). It serves a dual purpose: (1) the ASF cleans the spectrum of the fiber-delivered laser beam from any Raman signal generated by the fiber material (e.g. fused silica), so that monochromaticity of the laser light on sample is ensured; and (2) the ASF attenuates the spectrally unshifted light scattered by a sample and allows acquisition of the sample Raman spectrum by a fiber-coupled single stage spectrograph. Other ASF configurations (e.g. shown in FIG. 1) also could be used to achieve similar results. As shown in FIG. 10 according to the invention incorporation of an ASF 308 enables a spectroscopy system 300 for delivering filtered light from a fiber coupled source to a sample, collecting the light scattered from the sample, filtering that light and delivering the filtered light to a detector. The light source 302 is coupled via a fiber optic 304 to a collimating lens 306 that delivers this light to the ASF 308. The light, containing both shifted (produced in passage through the fiber optic's material) and unshifted wavelengths passes through the input polarizing beamsplitter cube 310 providing a linear polarized beam 312, then passes through a stack of at least one (six as shown) quartz plates 314 with orientations of their optic axis a previously stated. Light output 316 from the stack of quartz plates now contains a mixture of linear and elliptical polarized light and enters into a second polarizing beamsplitting cube 318 where the shifted wavelengths, added by passage through the input fiber, are rejected 320. The (now) monochromatic beam 322 is focused by a lens 324 onto a sample 326 and is scattered back along the original path. The backscattered light 328 contains both unshifted light and (Raman) shifted light of various polarization states that is recollimated by the focusing lens 324 and passed back into the ASF 308 where it passes through the beamsplitting cube 318 and emerges as a linearly polarized light beam 330. Passing through the quartz plate stack 314 the beam becomes a mixture of linear and elliptically polarized light 332 depending on wavelength. The unshifted light passes through the beamsplitting cube 310 while the wavelength shifted light 334, the light of interest, is diverted to a focusing lens 336 which couples this light into an optical fiber 338 that delivers the light to a spectrograph 340 for analysis. Thus both light input and output are fiber coupled and successfully delivered, filtered, and analyzed.

Although the above description covers the type and material of polarizers, birefringent plates and other components, it should be understood that a variety of alternative configurations and materials can be used, especially in the VIS-NIR ranges as the choice of materials is greatly expanded. Particularly, liquid-crystal polarizers or phase retarders which allow filter tunability are available for VIS-NIR. In much of the DUV spectral region (190-300 nm) no alternative notch filter exists.

Thus, while the present invention has been described with respect to exemplary embodiments thereof, it will be understood by those of ordinary skill in the art that variations and modifications can be effected within the scope and spirit of the invention.

What is claimed as new and desired to be protected by Letters Patent of the United States is:

1. An additive Šolc filter (ASF), comprising:
    a first polarizer having an input for receiving an input light and transmitting a first polarized light output;
    at least one birefringent plate positioned to receive the first polarized light output and transmit a second light output having a wavelength dependent state of polarization;
    a second polarizer for receiving the second light output and transmitting a third polarized, filtered light output; and
    wherein the first polarizer, the at least one birefringence plate, and the second polarizer each have a selected relative position and orientation such that the at least one birefringement plate second light output includes at least one or more wavelengths polarized so that they are selectively rejected by the second polarizer from the third light output and by which the ASF thereby operates as a narrow-line wavelength rejection (notch) filter with the third polarized, filtered light output thereby comprising a narrow-line additive wavelength transmission output.

2. The filter of claim 1, further comprising a plurality of birefringent plates.

3. A spectroscopy system, comprising:
a monochromatic light source input;
an additive Šolc filter (ASF) comprising:
a first polarizer having an input for receiving an input light and transmitting a first polarized light output;
at least one birefringent plate positioned to receive the first polarized light output and transmit a second light output having a wavelength dependent state of polarization;
a second polarizer for receiving the second light output and transmitting a third polarized, filtered light output, and wherein the first polarizer, the at least one birefringement plate, and the second polarizer each have a selected relative position and orientation such that the at least one birefringement plate second light output includes at least one or more wavelengths polarized so that they are selectively rejected by the second polarizer from the third light output and by which the ASF thereby operates as a narrow-line wavelength rejection (notch) filter with the third polarized, filtered light output thereby comprising a narrow-line additive wavelength transmission output;
a sample chamber for exposing a sample to the third light output and generating a filtered signal characteristic of the sample; and
a detector for acquiring the filtered characteristic signal.

4. A spectroscopy system as in claim 3, wherein the ASF comprises a plurality of birefringent plates.

5. A spectroscopy system as in claim 4, wherein the spectroscopy system is tuned to the deep ultraviolet (DUV) frequency range.

6. A spectroscopy system as in claim 5, wherein the light source input is in the range of from about 190 nm to about 300 nm.

7. A spectroscopy system as in claim 6, wherein the spectroscopy system is tuned to measure Raman scattering.

8. A spectroscopy system as in claim 3, wherein the monochromatic light source is a laser.

9. A spectroscopy system, comprising:
a light source having an output;
a collimating lens having an input fiber-optically coupled to the light source input and having an output;
an additive Šolc filter (ASF), having an input fiber-optically coupled to the collimating lens output, comprising:
a first polarizer having an input for receiving an input light and transmitting a first polarized light output;
at least one birefringent plate positioned to receive the first polarized light output and transmit a second light output having a wavelength dependent state of polarization;
a second polarizer for receiving the second light output and transmitting a monochromatic light output, and wherein the first polarizer, the at least one birefringement plate, and the second polarizer each have a selected relative position and orientation such that the at least one birefringement plate second light output includes at least one or more wavelengths polarized so that they are selectively rejected by the second polarizer from the third light output and by which the ASF thereby operates as a narrow-line wavelength rejection (notch) filter with the monochromatic light output comprising a narrow-line additive wavelength transmission output;
a first focusing lens positioned along a common optical path with the ASF, for focusing the monochromatic light onto a sample, thereby producing a sample-light, containing both unshifted light and wavelength-shifted light of various polarization states, backscattered along the common optical path that is recollimated by the focusing lens into the ASF, producing a linearly polarized output light beam upon traversing the second polarizer, a mixture of linear and elliptically polarized light upon traversing the at least one birefringent plate, whereby the unshifted light exits the system;
a second focusing lens for receiving and focusing the wavelength-shifted light; and
a spectrograph fiber-optically coupled to the second lens for analyzing the focused, wavelength-shifted for analysis.

10. A spectroscopy system as in claim 9, wherein the ASF comprises a plurality of birefringent plates.

11. A spectroscopy system as in claim 10, wherein the spectroscopy system is tuned to the deep ultraviolet (DUV) frequency range.

12. A spectroscopy system as in claim 11, wherein the light source input is in the range of from about 190 nm to about 300 nm.

13. A spectroscopy system as in claim 12, wherein the monochromatic light source is a laser.

14. A spectroscopy system as in claim 13, wherein the spectroscopy system is tuned to measure Raman scattering.

15. A spectroscopy system as in claim 9, wherein the monochromatic light source is a laser.

* * * * *